United States Patent [19]

Fujioka et al.

[11] Patent Number: 4,546,192
[45] Date of Patent: Oct. 8, 1985

[54] CHLORINE EXCHANGE FOR FLUORINE IN RING-FLUORINATED PYRIDINE COMPOUNDS

[75] Inventors: George S. Fujioka, Walnut Creek; Alexander P. Fung, Pleasant Hill, both of Calif.

[73] Assignee: The Dow Chemical Company, Midland, Mich.

[21] Appl. No.: 422,318

[22] Filed: Sep. 23, 1982

[51] Int. Cl.[4] ............................................ C07D 213/26
[52] U.S. Cl. .................................... 546/345; 546/346
[58] Field of Search ................ 546/345; 570/145, 147, 570/170, 207, 208, 260, 210

[56] References Cited

U.S. PATENT DOCUMENTS

| 3,370,096 | 2/1968 | Donaldson et al. | 570/260 |
|---|---|---|---|
| 4,172,203 | 10/1979 | Ison | 546/345 |
| 4,493,932 | 1/1985 | Werner | 546/345 |

FOREIGN PATENT DOCUMENTS 725221  1/1966  Canada ............................ 570/147

OTHER PUBLICATIONS

Yakobson et al., J. Org. Chem. U.S.S.R., vol. 6, No. 7, (1970), pp. 1661–1662.

*Primary Examiner*—Joseph Paul Brust

[57] ABSTRACT

Ring-fluorinated pyridine compounds are contacted with a chlorinating agent, preferably in the presence of a catalyst, under favorable conditions to yield pyridine compounds having a chlorine substituted in the ring-fluorine position(s).

11 Claims, No Drawings

CHLORINE EXCHANGE FOR FLUORINE IN RING-FLUORINATED PYRIDINE COMPOUNDS

BACKGROUND OF THE INVENTION

The present invention relates to a method of exchanging chlorine atoms for fluorine atoms in ring-fluorinated pyridine compounds.

(Trifluoromethyl)pyridine compounds are commercially valuable chemical intermediates useful in the preparation of medicinal agents and agricultural chemicals. (Trifluoromethyl)pyridine compounds are generally prepared by fluorinating a (trichloromethyl)pyridine compound.

Problems associated with the preparation of (trifluoromethyl)pyridine compounds include (1) an over fluorinated end product, i.e., ring-fluorinated, (trifluoromethyl)pyridines and (2) the formation of a ring-fluorinated isomer of the desired (trifluoromethyl)pyridine product generally described as a fluoro-(chlorodifluoromethyl)pyridine compound. These ring-fluorinated by-products reduce the yield of the desired (trifluoromethyl)pyridines and necessitate additional separatory procedures which are both bothersome and expensive. The ring-fluorinated isomer is a particularly annoying by-product because of the difficulty in separating it from the desired (trifluoromethyl)pyridine product.

EPO Application No. 80201077.7 (Publication number: 0 028,870) teaches the preparation of 2-chloro-5-(trifluoromethyl)pyridine compounds employed as intermediates in the preparation of 2-pyridinyloxy(or thio)phenoxy alkanoic acids and derivatives thereof which are herbicides. It discloses that the formation of the 2-fluoro pyridine is of no practical disadvantage since the halogen at the 2-position is displaced in the subsequent reaction with the metal salt of the hydroxy phenoxy alkanoic acid compound. However, having a fluoro in the 2-pyridine ring position poses a waste stream problem with a metal fluoride (KF, NaF) when compared to a waste stream of NaCl or KCl when a chloro is in the 2-pyridine ring position. Furthermore, converting the 2-fluoro pyridine compounds to 2-chloro pyridine compounds according to the present invention allows for the recovery of HF which can be recycled for use as a fluorinating agent. It is clearly evident that there is a need for a method of converting the 2-fluoro-pyridine by-products to the desired 2-chloro-pyridine compounds.

Heretofore, a method of displacing fluorine atoms from a pyridine ring with a chlorine atom has not been disclosed.

SUMMARY OF THE INVENTION

Briefly, in accordance with the present invention, a pyridine compound, having at least one fluorine atom attached directly to the pyridine ring, is reacted with a chlorinating agent under conditions favorable to replace the fluorine atoms with chlorine atoms. The chlorinated products of this method are useful as intermediates in the synthesis of biologically active compounds, such as, medicinals and herbicides.

Of particular interest in the practice of this invention is a method of replacing the fluorine atom at the 2-ring position of 3-chloro-2-fluoro-5-(trifluoromethyl)pyridine with a chlorine atom yielding 2,3-dichloro-5-(trifluoromethyl)pyridine, an intermediate in the manufacture of agricultural chemicals.

Also of interest are methods of replacing the fluorine atoms at the 2- and/or 6-positions of 2-fluoro-5-(trifluoromethyl)pyridine; 2-chloro-6-fluoro-3-(trifluoromethyl)pyridine; 2,6-difluoro-3-(trifluoromethyl)pyridine; 2-fluoro-3-chloro-5-(chlorodifluoromethyl)pyridine; and 2-fluoro-5-(chlorodifluoromethyl)pyridine with a chlorine atom yielding chlorinated-5-(trifluoromethyl)- or (chlorodifluoromethyl)-pyridine compounds.

DETAILED DESCRIPTION OF THE EMBODIMENTS

In conducting the present reaction, a pyridine compound, having a fluorine atom attached to the pyridine ring (hereinafter referred to as a "ring-fluorinated pyridine compound"), is contacted with a chlorinating agent at a temperature in the range of from about 80° C. to about 250° C. preferably in the presence of a metal halide catalyst, metal halide/phosphorus halide catalyst or mixtures thereof.

Ring-fluorinated pyridine compounds include 3-chloro-2-fluoro-5-(trifluoromethyl)pyridine; 2-fluoro-5-(trifluoromethyl)pyridine; 2,6-difluoro-3-(trifluoromethyl)pyridine; 2-chloro-6-fluoro-3-(trifluoromethyl)pyridine; and the above compounds wherein -chlorodifluoromethyl or -dichlorofluoromethyl groups are substituted for the trifluoromethyl groups. The ring-fluorinated pyridine compounds can be reacted separately or as a mixture containing more than one ring-fluorinated pyridine compound.

In a preferred embodiment, a mixture, containing chlorinated (trifluoromethyl)pyridines and one or more ring-fluorinated pyridine compounds, is reacted according to the present invention whereby a chlorine atom is exchanged for the fluorine atom attached to the pyridine ring. The above mixtures are advantageously obtained from the reaction products in the preparation of (trifluoromethyl)pyridine compounds whereby the ring-fluorinated pyridine compounds are undesirable by-products.

The employment of a chlorinating agent is a critical component of the present invention and $FeCl_3$ and HCl are suitably employed, with HCl being preferred. Suitable chlorinating agents are preferably supplied in amounts to provide at least about one mole of chlorine atoms per mole of fluorine atoms to be displaced on the ring-fluorinated pyridine compounds. While an excess of chlorinating agent can be employed, it is not detrimental to the present process.

In practicing the present invention, it is preferred to employ a metal halide catalyst or a metal halide/phosphorus halide catalyst. Mixtures of catalysts may also be employed. Suitable metal halides include metal chlorides, such as, $FeCl_3$, $SnCl_4$, $TiCl_4$, $TaCl_5$, $WCl_6$, $NbCl_5$ and $CrCl_3$ and metal fluorides, such as, $FeF_3$, $SnF_4$ and $CrF_2$. Preferred catalysts include $FeCl_3$ (anhydrous) and $FeF_3$. The catalysts are present in an amount sufficient to cause accelerated substitution of a chlorine atom for a fluorine atom attached to the pyridine ring, hereinafter referred to as "catalytic" amount. Generally, a catalytic amount is present when from about 0.1 to about 20 mole percent, based on the total moles of ring-fluorinated pyridine compounds, of catalyst is added to the present reaction mixture and advantageously from about 0.25 to about 10 mole percent. A preferred amount of catalyst to be present in the present reaction is about 5 mole percent.

Generally, the present reaction is conducted neat, although a solvent, such as, benzene or xylene, may be employed.

The present reaction is advantageously conducted in the liquid phase at a temperature of between about 80° C. to about 250° C. and preferably between about 160° C. and about 185° C. A particularly preferred temperature to conduct the present reaction is about 170° C. The present reaction is typically conducted in the presence of agitation sufficient to thoroughly contact the reactants.

In conducting the present reaction, neither the rate of addition of the chlorinating agent nor the order of addition of the reactants is critical. Preferably, the suitable chlorinating agent is added in gaseous form to the other reactants. In the usual case, the ring-fluorinated pyridine compounds and catalyst are mixed before the chlorinating agent is added. A typical reaction according to the present invention generally requires from about ½ to about 48 hours to be substantially complete.

While the pressure at which the present reaction is conducted is not critical, superatmospheric pressures, due to the increased temperatures and the chlorinating agent, are seen when the reaction is conducted in a contained vessel.

The present reaction can be characterized as follows:

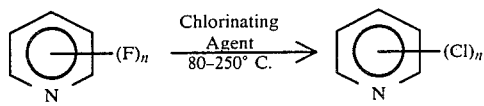

wherein n represents 1, 2 or 3. The pyridine ring may optionally contain other substituents besides the —F, such as, —Cl, CCl$_3$, —CF$_3$, —CClF$_2$ and —CCl$_2$F. Of particular interest are reactions involving pyridine compounds which contain a fluoro atom attached to the pyridine ring in the 2 and/or 6 position and which are characterized as follows:

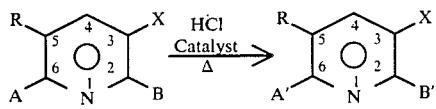

wherein
R represents —H, —CF$_3$, —CF$_2$Cl, —CCl$_2$F, or CCl$_3$
X represents Cl or H;
A ad B each independently represent H, Cl or F with the proviso that at least one of A and B is always F;
A' represents Cl when A is Cl or F and A' represents H when A is H; and
B' represents Cl when B is Cl or F and B' represents H when B is H.

Especially preferred reactions are characterized as follows:

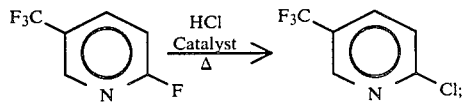

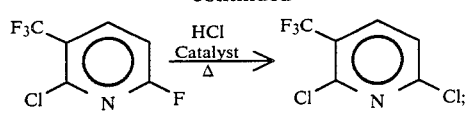

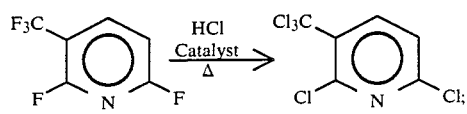

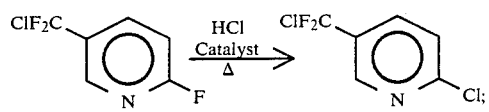

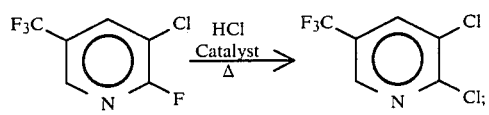

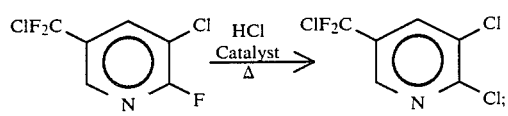

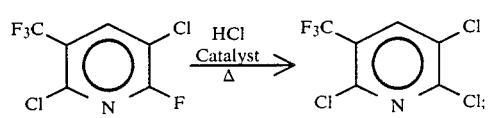

and

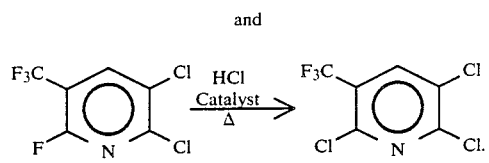

In a preferred embodiment of the present invention, the reaction product in the preparation of 2-chloro-5-(trifluoromethyl)pyridine, which contains 2-fluoro-pyridines, such as, 2-fluoro-5-(trifluoromethyl)pyridine and 2-fluoro-5-(chlorodifluoromethyl)pyridine, in addition to the desired 2-chloro-5-(trifluoromethyl)pyridine and metal halide catalysts, is contacted with HCl at elevated temperatures as described herein to convert the 2-fluoro-pyridines to their corresponding 2-chloro analogs. The desired 2-chloro-5-(trifluoromethyl)pyridine is then readily separable from the reaction mixture by distillation since the 2-fluoro isomer, i.e. 2-fluoro-5-(chlorodifluoromethyl)pyridine, is converted to 2-chloro-5-(chlorodifluoromethyl)pyridine which has a boiling point different from the desired product. The catalyst may be added separately or may be already present in reaction product mixture as a catalyst in the preparation of 2-chloro-5-(trifluoromethyl)pyridine.

In an especially preferred embodiment of the present invention, the reaction product in the preparation of 2,3-dichloro-5-(trifluoromethyl)pyridine, which contains 2-fluoro-pyridines, such as, 3-chloro-2-fluoro-5-(trifluoromethyl)pyridine and 3-chloro-2-fluoro-5-(chlorodifluoromethyl)pyridine, in adddition to the desired 2,3-dichloro-5-(trifluoromethyl)pyridine and metal halide catalysts, is contacted with HCl at elevated temperatures as described herein to convert the 2-fluoro-pyridines to their corresponding 2-chloro analogs. The desired 2,3-dichloro-5-(trifluoromethyl)pyridine is then readily separable from the reaction mixture by distillation since the 2-fluoro isomer, i.e., 3-chloro-2-fluoro-5-(chlorodifluoromethyl)pyridine, is converted to 2,3-dichloro-5-(chlorodifluoromethyl)pyridine which has a boiling point different from the desired product. The catalyst may be added separately or may be already present in the reaction product mixture as a catalyst in the preparation of 2,3-dichloro-5-(trifluoromethyl)pyridine.

The following examples illustrate the practice of the present invention but should not be construed as limiting its scope.

EXAMPLE 1

To a high pressure nickel reactor were added 8 grams of a mixture containing 92.6 percent by weight 3-chloro-2-fluoro-5-(trifluoromethyl)pyridine, 4.5 percent by weight 2,3-dichloro-5-(trifluoromethyl)pyridine and 2.9 percent by weight unidentified related compounds. To this mixture was added 0.7 g $FeCl_3$ (anhydrous). The reactor was then pressurized to 80 psi with anhydrous HCl at room temperature. The mixture was then heated to 180° C. with rocking agitation for 20 hours. After cooling to room temperature, the excess pressure was released. The reactor was opened and the contents analyzed by standard gas-liquid chromatography (GLC) procedures. The results indicated the resulting product contained 83.5 percent by weight 2,3-dichloro-5-(trifluoromethyl)pyridine, 11.8 percent by weight 3-chloro-2-fluoro-5-(trifluoromethyl)pyridine and the balance unidentified by-product.

EXAMPLE 2

A 200 ml PERFLUOROALKOXY ® (PFA) reaction flask fitted with a PFA reflux condenser, an HCl bleed tube, a magnetic stirrer and an optical pyrometer was charged with 60 g of a mixture containing 54.8 percent by weight 3-chloro-2-fluoro-5-trifluoromethyl)-pyridine and 45.2 percent by weight 2,3-dichloro-5-(trifluoromethyl)pyridine and 2.25 g of $FeCl_3$ (5 mole percent). Anhydrous HCl gas was introduced into the reaction mixture below the surface of the liquid of the mixture was heated to a temperature of 170° C. This temperature was maintained for a period of 15 hours after which the reaction mixture was quenched with 40 g of ice. The organic layer was separated, neutralized with $NaHCO_3$ and dried over $Na_2SO_4$. Analysis of the product indicated that it contained 68.5 percent by weight 2,3-dichloro-5-(trifluoromethyl)pyridine, 5 percent by weight 3-chloro-2-fluoro-5-(trifluoromethyl)-pyridine and 26.4 percent 2,3-dichloro-5-(chlorodifluoromethyl)pyridine.

EXAMPLE 3

A 335 ml nickel reaction vessel, equipped with a mechanical agitator, nickel reflux condenser and an HCl bleed tube, was charged with 105 g of 3-chloro-2-fluoro-5-(trifluoromethyl)pyridine and 7.5 g of anhydrous $FeCl_3$. Anhydrous HCl gas was continuously sparged into the reaction mixture at a rate of about 25 ml/min throughout the reaction. The temperature of the reaction mixture was kept between 140° and 160° C. for 22.5 hours. The reaction mixture was quenched with 100 ml of ice water. The organic layer was separated, neutralized with $NaHCO_3$ and dried over $MgSO_4$. Analysis of the resulting product employing standard GLC procedures indicated 86 percent by weight was 2,3-dichloro-5-(trifluoromethyl)pyridine which was then isolated in a pure form by distillation.

EXAMPLE 4

A 335 ml nickel vessel was charged with 105 g of a mixture containing 88 percent by weight 2,3-dichloro-5-(trifluoromethyl)pyridine and 12 percent by weight 3-chloro-2-fluoro-5-(chlorodifluoromethyl)pyridine and 7 g of anhydrous $FeCl_3$. Anhydrous HCl gas was continuously sparged into the reaction mixture at a rate of about 20 ml/min as the mixture was heated to a temperature of 170° C. and maintained at this temperature for 7 hours. The reaction mixture was quenched with 100 ml of ice water. The organic layer was separated, washed twice with 100 ml of water, neutralized with $NaHCO_3$ and dried over $MgSO_4$. Standard GLC analysis indicated the resulting product contained 90.1 percent by weight 2,3-dichloro-5-(trifluoromethyl)pyridine, 0.5 percent by weight 3-chloro-2-fluoro-5-(chlorodifluoromethyl)pyridine, 2.2 percent by weight 3-chloro-2-fluoro-5-(trifluoromethyl)pyridine and 7.2 percent by weight 2,3-dichloro-5-(chlorodifluoromethyl)pyridine.

EXAMPLE 5

A 480 ml Teflon ®-PFA reaction flask, fitted with a PFA reflux condenser, an HCl bleed tube, a magnetic stirrer and an optical pyrometer, was charged with 8.25 g of anhydrous $FeCl_3$ and 165 g of a reaction mixture containing 42.3 percent by weight 2,3-dichloro-5-(trifluoromethyl)pyridine, 7.1 percent by weight 3-chloro-2-fluoro-5-(chlorodifluoromethyl)pyridine, 10.7 percent by weight of 3-chloro-2-fluoro-5-(trifluoromethyl)pyridine, and 31 percent by weight 2,3-dichloro-5-(chlorodifluoromethyl)pyridine. Anhydrous HCl gas was continuously sparged into this reaction mixture at a rate of about 25 ml/min as the mixture was heated to a temperature of 163° C. and maintained for 9 hours. The reaction mixture was cooled and quenched with 200 ml of ice water. The organic layer was separated, neutralized with $NaHCO_3$ and dried over $MgSO_4$. Analysis of the resulting product employing standard GLC procedures indicated the product contained 59.8 percent by weight 2,3-dichloro-5-(trifluoromethyl)pyridine, 0.92 percent by weight 3-chloro-2-fluoro-5-(chlorodifluoromethyl)pyridine, 2.4 percent by weight 3-chloro-2-fluoro-5-(trifluoromethyl)pyridine and 30.7 percent by weight 2,3-dichlor-5-(chlorodifluoromethyl)pyridine.

EXAMPLE 6

Employing substantially the same procedure of Example 5, 105 g of 3-chloro-2-fluoro-5-(trifluoromethyl)-pyridine was heated at atmospheric pressure to 138° C. for 23 hours while HCl was continuously introduced into the flask at a rate of between 25–30 ml/min. No catalyst was employed. Six (6) samples were withdrawn from the flask at various times for analysis, the results of which are listed in Table 1.

TABLE 1

| Sample | Time Sample was Taken (hr) | 3-Chloro-2-fluoro-5-(trifluoromethyl)-pyridine Starting Material (Percent by Weight) | 2,3-Dichloro-5-(trifluoromethyl)pyridine (Percent by Weight) |
|---|---|---|---|
| 1 | 2 | 98.8 | 1.2 |
| 2 | 6 | 98.1 | 1.9 |
| 3 | 10 | 97.2 | 2.8 |

TABLE 1-continued

| Sample | Time Sample was Taken (hr) | 3-Chloro-2-fluoro-5-(trifluoromethyl)-pyridine Starting Material (Percent by Weight) | 2,3-Dichloro-5-(trifluoromethyl)pyridine (Percent by Weight) |
|---|---|---|---|
| 4 | 14 | 97.3 | 2.9 |
| 5 | 19 | 96.2 | 3.8 |
| 6 | 23 | 95.6 | 4.2 |

EXAMPLE 7

Employing substantially the same procedures of Example 5, 105 g of 3-chloro-2-fluoro-5-(trifluoromethyl)-pyridine and 5.4 ml of SnCl₄ (9.5 mole percent) were mixed and heated at atmospheric pressure to 110° C. for 13.5 hours while HCl was continuously introduced into the flask at a rate of between 25–30 ml/min. Analysis indicated the resulting product contained 58.2 percent by weight 2,3-dichloro-5-(trifluoromethyl)pyridine and 41.8 percent by weight starting material.

EXAMPLE 8

A mixture containing 105 g of 3-chloro-2-fluoro-5-(trifluoromethyl)pyridine and 9.3 g of FeCl₃ was heated to 138°–140° C. at atmospheric pressure for 10.5 hours with constant agitation. Analysis indicated about 8 percent of 3-chloro-2-fluoro-5-(trifluoromethyl)pyridine was converted to 2,3-dichloro-5-(trifluoromethyl)pyridine.

EXAMPLE 9

The reaction product mixture from the preparation of 2,3-dichloro-5-(trifluoromethyl)pyridine, made by fluorinating 2,3-dichloro-5-(trichloromethyl)pyridine with HF and 5 mole % FeCl₃, in the liquid phase, was heated to reflux (145° C.–170° C.) at atmospheric pressure. HCl gas was bubbled into the mixture at a rate of 25–30 cc/min. The initial composition of the mixture is indicated at time "0" in Table 2 in weight percent. The final composition of the mixture is indicated in sample 9 in Table 2 after a 54 hour reaction period.

EXAMPLE 10

Substantially the same procedure of Example 9 was employed except 2 mole % FeCl₃ was used in the fluorination reaction of 2,3-dichloro-5-(trichloromethyl)pyridine. The components of the reaction mixture before and after the reaction (170° C., for 28 hours; atmospheric pressure; HCl@25-30 cc/min.) are listed below in percentages (G.C. area percent):

| Component | Before | After |
|---|---|---|
| 2,3-dichloro-5-(trifluoromethyl)-pyridine | 50.4% | 76.9% |
| 3-Chloro-2-fluoro-5-(trifluoromethyl)pyridine | 30.9% | 2.0% |
| 3-chloro-2-fluoro-5-(chlorodifluoromethyl)pyridine | 4.3% | trace |
| 2,3-dichloro-5-(chlorodifluoromethyl)pyridine | 7.6% | 5.9% |
| 2,3-dichloro-5-(dichlorofluoromethyl)pyridine | 0.9% | 1.3% |

On repeating the above procedures using other substituted ring-fluorinated pyridine compounds and mixtures thereof, described herein as starting materials, substantially the same results are obtained, i.e., chloro displaces the ring-fluoro. Additionally, the present reaction is conducted as a continuous process whereby similar results are obtained.

What is claimed is:

1. A method of exchanging a chlorine atom for a fluorine atom in a ring-fluorinated pyridine compound which comprises contacting a ring-fluorinated pyridine compound of the formula

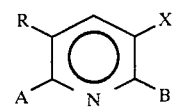

wherein

R represents —H, —CF₃, —CF₂Cl, CCl₂F or —CCl₃;

X represents Cl or H; and

A and B each independently represent H, Cl or F with the proviso that at least one of A and B is always F;

with an FeCl₃ and/or HCl chlorinating agent in the presence of a metal halide catalyst selected from FeCl₃,

TABLE 2

| | | Compounds Present in Mixture in Weight Percent | | | |
|---|---|---|---|---|---|
| Sample | Time (hr) | F₃C-pyridine-F | F₃C-pyridine-Cl,Cl | F₂ClC-pyridine-F | F₂ClC-pyridine-Cl,Cl |
| | 0 | 81.5 | 9.9 | 4.4 | 0.8 |
| 1 | 2 | 79.0 | 11.4 | 4.2 | 0.9 |
| 2 | 4 | 75.5 | 15.5 | 4.0 | 1.1 |
| 3 | 10 | 65.4 | 25.3 | 3.3 | 1.5 |
| 4 | 14 | 53.3 | 38.0 | 1.9 | 2.2 |
| 5 | 27 | 19.2 | 70.8 | 1.1 | 4.6 |
| 6 | 32 | 14.7 | 74.3 | 0.3 | 4.7 |
| 7 | 46 | 9.0 | 78.3 | —* | 4.9 |
| 8 | 50 | 8.2 | 78.0 | —* | 5.0 |
| 9 | 54 | 7.7 | 75.8 | —* | 4.6 |

*None detected.

SnCl₄, TiCl₄, TaCl₅, WCl₆, NbCl₅, CrCl₃, FeF₃, SnF₄ and CrF₂, or mixtures thereof at a temperature of at least about 80° F. at a pressure of from atmospheric to 80 psig with the proviso that when used as a catalyst FeCl₃ is employed in an amount in the range of from about 0.1 to about 20 mol percent based on mols of ring-fluorinated pyridine compounds and when used as a chlorinating agent FeCl$_3$ is used in an amount sufficient to provide at least about one mol of chlorine atoms per mol of fluorine atoms to be displaced.

2. Method of claim 1 wherein said chlorinating agent is HCl.

3. Method of claim 1 wherein said ring-fluorinated pyridine compound is 3-chloro-2-fluoro-5-(trifluoromethyl)pyridine; 3-chloro-2-fluoro-5-(chlorodifluoromethyl)pyridine; 3-chloro-2-fluoro-5-(dichlorofluoromethyl)pyridine or mixtures thereof and said reaction is conducted at a temperature in the range of from about 160° C. to about 185° C.

4. Method of claim 3 wherein said metal halide catalyst is FeCl$_3$, FeF$_3$, WCl$_6$, SnCl$_4$ or mixtures thereof.

5. Method of claim 4 wherein said catalyst is FeCl$_3$.

6. Method of claim 1 wherein said ring-fluorinated pyridine compound is 2-fluoro-5-(trifluoromethyl)pyridine; 2-chloro-6-fluoro-3-(trifluoromethyl)pyridine; 2,6-difluoro-5-(trifluoromethyl)pyridine; 2-fluoro-5-(chlorodifluoromethyl)pyridine or mixtures thereof and said reaction is conducted at a temperature in the range of from about 160° C. to about 185° C.

7. Method of claim 6 wherein said metal halide catalyst is FeCl$_3$.

8. Method of claim 1 wherein said ring-fluorinated pyridine compounds are obtained as reaction products in the preparation of 2-chloro-5-(trifluoromethyl)pyridine or 2,3-dichloro-5-(trifluoromethyl)pyridine.

9. Method of claim 8 wherein said contacting is conducted at a temperature in the range of from about 160° C. to about 185° C.

10. Method of claim 9 wherein said catalyst is present in an amount in the range of from about 0.1 to about 20 mol percent based on mols of ring-fluorinated pyridine compounds present in the reaction.

11. Method of claim 1 wherein the reaction is carried out at atmospheric pressure.

* * * * *

UNITED STATES PATENT AND TRADEMARK OFFICE
CERTIFICATE OF CORRECTION

PATENT NO. : 4,546,192
DATED : October 8, 1985
INVENTOR(S) : George S. Fujioka and Alexander P. Fung It is certified that error appears in the above-identified patent and that said Letters Patent is hereby corrected as shown below:

Column 3, line 54, "A ad B" should read --A and B--.

Column 5, line 38, "3-chloro-2-fluoro-5-trifluoromethyl)-" should read --3-chloro-2-fluoro-5-(trifluoromethyl)- --

Column 5, line 42, "liquid of the" should read --liquid as the--.

Column 8, line 65, "about 80°F. at" should read --about 80°C. at--.

Signed and Sealed this

Eleventh Day of March 1986

[SEAL]

Attest:

DONALD J. QUIGG

Attesting Officer    Commissioner of Patents and Trademarks